(12) United States Patent
Graf

(10) Patent No.: US 7,335,188 B2
(45) Date of Patent: Feb. 26, 2008

(54) LUMBAR PUNCTURE FLUID COLLECTION DEVICE

(76) Inventor: Christian D. Graf, 340 Bermuda Towne Row, Mt. Pleasant, SC (US) 29464

( * ) Notice: Subject to any disclaimer, the term of this patent is extended or adjusted under 35 U.S.C. 154(b) by 530 days.

(21) Appl. No.: 10/866,572

(22) Filed: Jun. 12, 2004

(65) Prior Publication Data

US 2005/0277848 A1 Dec. 15, 2005

(51) Int. Cl.
*A61M 1/00* (2006.01)
*B67C 3/00* (2006.01)

(52) U.S. Cl. .................. 604/317; 211/74; 220/23.87; 600/573; 600/575

(58) Field of Classification Search ............... 604/317; 220/23.87, 23.88, 23.89; 211/77, 80, 81; 60/575; 99/413
See application file for complete search history.

(56) References Cited

U.S. PATENT DOCUMENTS

| 211,076 | A | * | 12/1878 | Follett | 99/413 |
|---|---|---|---|---|---|
| 1,763,461 | A | * | 6/1930 | Fowler | 422/104 |
| 2,004,150 | A | * | 6/1935 | Zander | 96/334 |
| 2,046,864 | A | * | 7/1936 | Baker | 422/104 |
| 2,563,141 | A | * | 8/1951 | Vazzano | 62/331 |
| 2,563,352 | A | * | 8/1951 | Morse | 206/515 |
| 2,679,067 | A | * | 5/1954 | Delmas | 15/263 |
| 3,196,909 | A | * | 7/1965 | Monk | 141/237 |
| 3,405,706 | A | | 10/1968 | Cinqualbre | |
| 3,494,351 | A | | 2/1970 | Horn | |
| 3,713,583 | A | * | 1/1973 | Gruber | 239/17 |
| 3,752,651 | A | * | 8/1973 | Bush | 436/177 |
| 3,790,029 | A | * | 2/1974 | Ward | 222/129.4 |
| 3,794,088 | A | * | 2/1974 | Harvey | 141/237 |
| 3,811,136 | A | * | 5/1974 | Whitney et al. | 600/573 |
| 3,922,913 | A | * | 12/1975 | Scott | 73/219 |
| 4,106,490 | A | * | 8/1978 | Spilman et al. | 600/574 |
| 4,453,576 | A | * | 6/1984 | Burns | 141/168 |
| 4,733,680 | A | * | 3/1988 | Mosier | 141/31 |
| 4,981,144 | A | * | 1/1991 | Carels, Jr. | 600/573 |
| 4,982,850 | A | * | 1/1991 | Mears | 211/74 |
| 5,092,378 | A | * | 3/1992 | Dunham | 141/237 |
| 5,097,842 | A | | 3/1992 | Bonn | |
| 5,326,032 | A | * | 7/1994 | Quillin | 239/20 |
| 5,330,439 | A | * | 7/1994 | Jackson | 604/192 |
| 5,380,289 | A | * | 1/1995 | Hemstreet et al. | 604/317 |
| 5,429,803 | A | * | 7/1995 | Guirguis | 422/58 |
| 5,484,002 | A | * | 1/1996 | Kupietzky | 141/237 |
| 5,498,395 | A | * | 3/1996 | Moore et al. | 422/100 |

(Continued)

*Primary Examiner*—Tatyana Zalukaeva
*Assistant Examiner*—Paula L. Craig
(74) *Attorney, Agent, or Firm*—Harleston Law Firm LLC

(57) ABSTRACT

A device for collecting spinal fluid during a lumbar puncture or other medical procedure includes: a) an upper, generally cup-shaped portion including an open top, an upper cup side wall, an upper cup base plate at a lower end of the upper cup side wall, and a drain hole in the upper cup base plate; b) a lower, generally cup-shaped portion including an open top, a lower cup side wall, and a lower cup base plate at a lower end of the lower cup side wall, the lower cup base plate including a plurality of generally circular openings; wherein the upper, generally cup-shaped portion is removably insertable in and rotatable in the lower, generally cup-shaped portion, and the upper, generally cup-shaped portion includes a rotation mechanism for rotating the upper, generally cup-shaped portion in the lower cup-shaped portion.

19 Claims, 11 Drawing Sheets

U.S. PATENT DOCUMENTS

| | | |
|---|---|---|
| 5,505,721 A | 4/1996 | Leach et al. |
| 5,624,404 A * | 4/1997 | Fisler ................... 604/187 |
| 5,772,607 A | 6/1998 | Magram |
| 5,785,662 A | 7/1998 | Alexander |
| 5,911,253 A * | 6/1999 | Webb .................... 141/243 |
| 5,951,524 A * | 9/1999 | Enriquez ................ 604/192 |
| 6,103,291 A * | 8/2000 | Fernandez Tapia ...... 426/523 |
| 6,158,484 A * | 12/2000 | Greenlee ................ 141/242 |
| 6,171,261 B1 * | 1/2001 | Niermann et al. ........ 600/573 |
| 6,235,010 B1 * | 5/2001 | Wilkinson et al. ....... 604/356 |
| 6,251,686 B1 * | 6/2001 | Studer et al. ............ 436/180 |
| 6,352,168 B1 * | 3/2002 | Lin ....................... 220/592.17 |
| 6,358,232 B1 * | 3/2002 | Hand et al. ............. 604/319 |
| 6,375,027 B1 | 4/2002 | Thomas et al. |
| 6,543,100 B1 * | 4/2003 | Finley et al. ............ 24/555 |
| 6,846,293 B2 * | 1/2005 | Butler et al. ............ 600/573 |
| 7,114,403 B2 * | 10/2006 | Wu et al. ................ 73/864.72 |
| 2002/0011492 A1 * | 1/2002 | Iskra ..................... 220/23.87 |
| 2002/0068882 A1 * | 6/2002 | Butler et al. ............ 600/573 |
| 2003/0071040 A1 * | 4/2003 | Brodner et al. ......... 220/23.87 |
| 2004/0147878 A1 * | 7/2004 | Lyon et al. ............. 604/192 |
| 2005/0180882 A1 * | 8/2005 | Tung et al. ............. 422/61 |

* cited by examiner

LUMBAR PUNCTURE FLUID COLLECTION DEVICE

BACKGROUND OF THE INVENTION

1. Technical Field

The present invention relates to a fluid collection device for holding several test tubes, which successively receive spinal fluid from a lumbar puncture or other medical procedure.

2. Background Information

One uncomfortable medical procedure that is often performed by a physician to diagnose illnesses such as meningitis or relieve pressure in the spinal column and brain is a lumbar puncture. During the lumbar puncture procedure, the patient sits or lies in a fetal position on a hospital table while the physician inserts a relatively large bore needle between two lumbar vertebrae in the patient's lower back. If the physician's aim is good, spinal fluid will immediately begin to drip from the needle bore. The spinal fluid will then continue dripping until the needle is removed from the spine.

In a standard lumbar puncture procedure, the physician holds a series of test tubes under the dripping spinal fluid, one at a time, until each test tube fills with several cubic centimeters of fluid. Laboratories usually require four test tubes of spinal fluid from an adult patient, and three tubes when the patient is a child. Unfortunately, spinal fluid is often lost as the test tubes are switched. The physician must place the first, full tube carefully in a test tube holder, while picking up the empty second tube and holding it under the dripping needle. Once the second test tube fills, this procedure is repeated for the third and fourth test tubes. Even if this is done as quickly as possible, significant amounts of spinal fluid can be lost during the test tube exchange. Since the spine is a particularly sensitive area of the body, it would be quite beneficial to the patient, the physician, and the hospital if something could be done to lessen discomfort for the patient and speed this process along.

BRIEF SUMMARY OF THE INVENTION

The present invention is a device for collecting spinal fluid during a lumbar puncture procedure or the like. The present fluid collection device includes:
  a) an upper, generally cup-shaped portion comprising an open top, an upper cup side wall, an upper cup base plate at a lower end of the upper cup side wall, and a drain hole in the upper cup base plate;
  b) a lower, generally cup-shaped portion comprising an open top, a lower cup side wall, and a lower cup base plate at a lower end of the lower cup side wall, the lower cup base plate comprising a plurality of generally circular openings;
  wherein the upper, generally cup-shaped portion is removably insertable in and rotatable in the lower, generally cup-shaped portion, and the upper, generally cup-shaped portion comprises a rotation mechanism for rotating the upper, generally cup-shaped portion in the lower cup-shaped portion.

Advantages of the present fluid collection device include the following: 1) less spinal fluid is wasted; 2) the entire lumbar puncture procedure is easier and takes less time, which benefits the patient, the physician, and the hospital; 3) there is less likelihood of local infection at the puncture site, since the needle is not in the patient for as long a period; 4) the collection device can be held and operated with one hand, leaving the other hand free for managing the patient, etc.; and 5) the physician is not concentrating on exchanging loose test tubes, so he or she is free to pay attention to the patient, the needle, etc.

Also, the instant collection device facilitates a clean collection of spinal fluid. A clean collection is desirable, as it reduces the likelihood that contaminants will interfere with the laboratory tests that will be conducted on the fluid samples in the test tubes.

Another important advantage is that the present collection device can be carried with the test tubes still attached to it down to the hospital or clinic laboratory; hence, it is unlikely that the group of four or so test tubes will be separated in transit to the laboratory or in the laboratory, or that the test tubes will be mislabeled or lose their labels, which unfortunately does occur in hospital laboratories. Laboratory error can have adverse consequences, including misdiagnosis, which can even cause death. The collection device of the present invention permits one label to be used for the entire device, or, alternatively, a separate label for each of the four individual test tubes. Since the test tubes are kept together by the device, the potential for laboratory error is reduced.

BRIEF DESCRIPTION OF THE SEVERAL VIEWS OF THE DRAWINGS

A more complete understanding of the invention and its advantages will be apparent from the following detailed description taken in conjunction with the accompanying drawings, wherein examples of the invention are shown, and wherein.

DETAILED DESCRIPTION OF THE INVENTION

Figure 1:
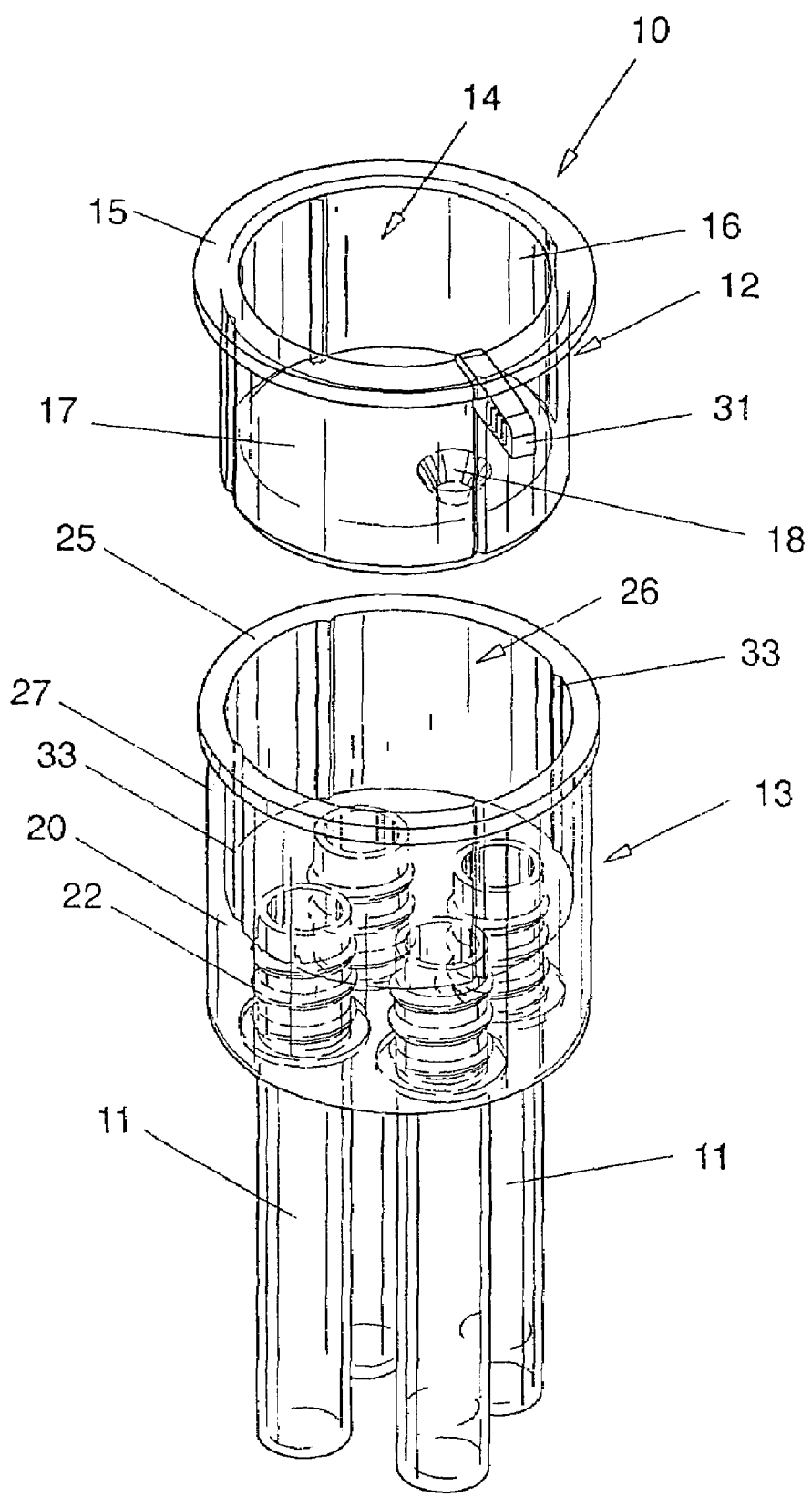
FIG. 1 is a perspective view of a lumbar puncture fluid collection device according to the present invention.

In the following description, like reference characters designate like or corresponding parts throughout the several views. Also, in the following description, it is to be understood that such terms as "inside," "outside," and the like are words of convenience and are not to be construed as limiting terms. Referring in more detail to the drawings, the invention will now be described.

Turning first to FIG. 1, a lumbar puncture fluid collection device 10 according to a first embodiment of the present invention supports four test tubes 11. The removable test tubes 11 are used for collecting a patient's spinal fluid, which drips from a relatively large bore needle that has been inserted in the patient's lower back in the course of a lumbar puncture medical procedure. As soon as the physician inserts the needle, she or he must hold or set the collection device 10 directly under the needle so that spinal fluid dripping from the needle falls into the collection device. The collection device 10 is comprised of an upper, generally cup-shaped ("upper cup") portion 12, which receives the fluid, and a lower, generally cup-shaped ("lower cup") portion 13, which supports the test tubes 11.

Figure 2:
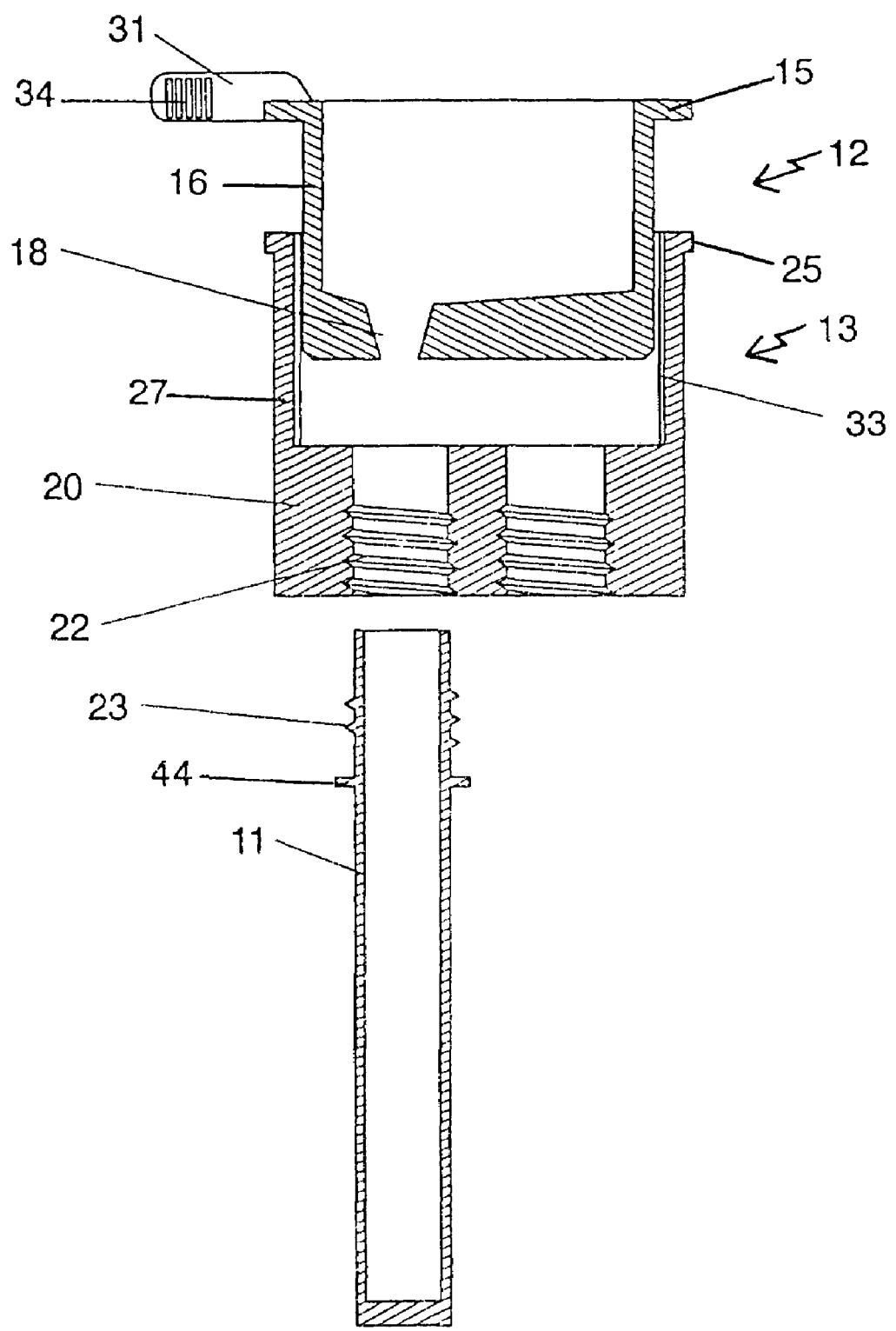
FIG. 2 is a cross-sectional, elevational view of a lumbar puncture fluid collection device according to the present invention, shown with a test tube.
Figure 3:
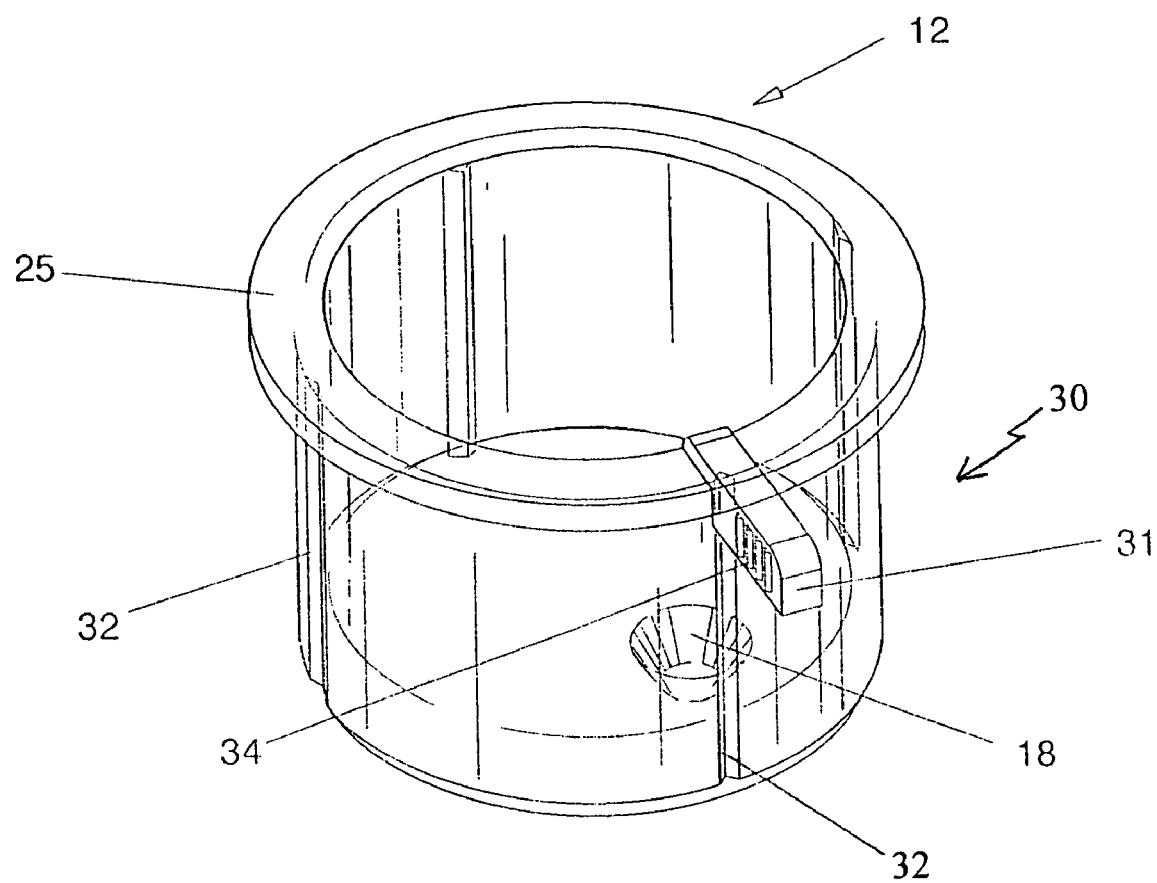
FIG. 3 is a perspective view of an upper portion of a lumbar puncture fluid collection device according to FIG. 1.

Referring to FIGS. 1 and 3, the upper cup portion 12 comprises an open top 14 surrounded by a generally circular upper cup lip 15, a substantially cylindrical upper cup side wall 16, and a generally circular upper cup base plate 17 at a bottom end of the upper cup portion 12. The upper cup base plate 17 includes a drain hole 18 that is positioned in a mid section of the base plate (i.e., not in the center or at the periphery of the base plate). The upper cup base plate 17 is sealed to, or integral with, the lower end of the upper cup side wall 16, so that any fluid contained in the upper cup portion 12 can only leave the upper cup portion 12 through the drain hole 18, or through the open top if the upper cup portion 12 were to be tipped over. The upper face of the upper cup base plate 17 is slightly sloped, most preferably two or three degrees, toward the drain hole 18 to encourage fluid in the upper cup to flow by gravity down the drain hole (see FIG. 2).

Figure 4:
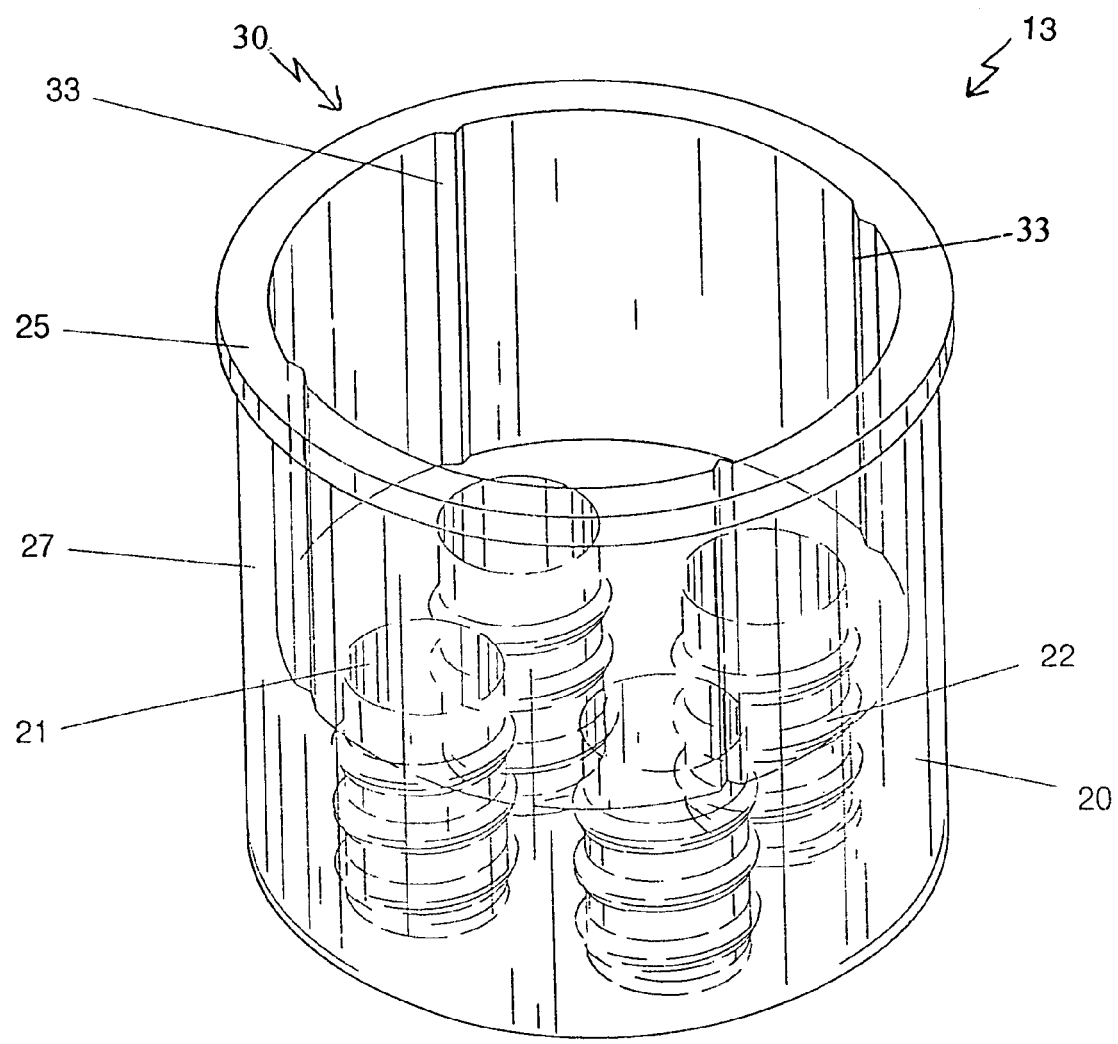
FIG. 4 is a perspective view of a lower portion of a lumbar puncture fluid collection device according to FIG. 1.
Figure 5:
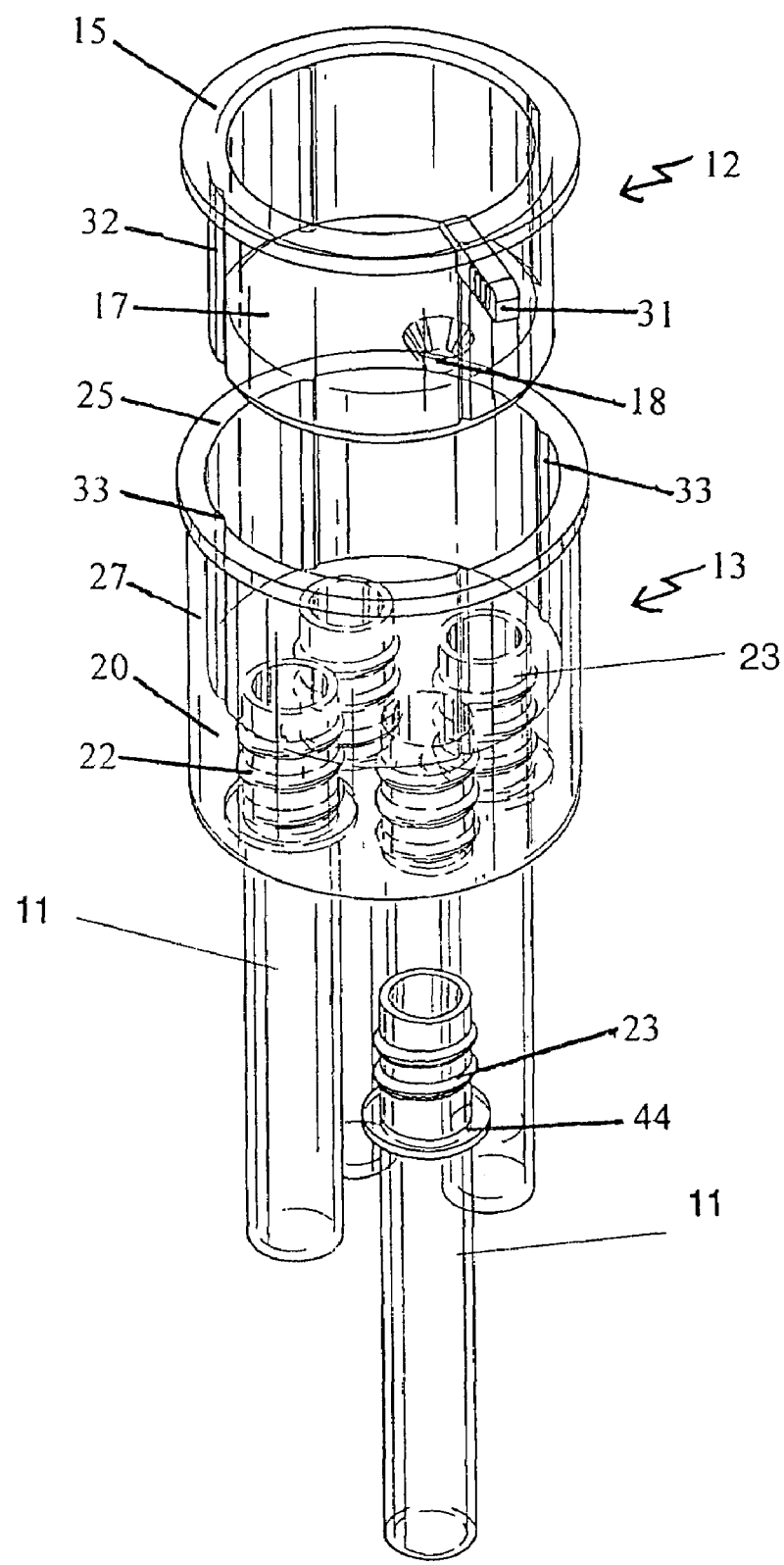
FIG. 5 is a perspective view of a lumbar puncture fluid collection device according to the present invention, shown with one test tube detached.

Referring to FIGS. 1, 2, and 4, the lower cup portion 13 also comprises a generally circular lower cup base plate 20, which has a number of generally circular, evenly spaced apart openings 21 for removably receiving a like number of test tubes 11. There are preferably four openings 21 for test tubes 11 in a collection device 10 for collecting spinal fluid from an adult. In the unusual case where more test tubes are needed, for example, for draining a relatively large amount of fluid from a patient with an abnormally high fluid pressure, a second collection device 10 may be used. Most standard sized test tubes are threaded at the top so that a correspondingly threaded cap (not shown) can be screwed on to close the test tube. As seen in FIG. 2, the wall of each opening 21 in the lower cup base plate 20 also includes threads 22 for receiving corresponding threads 23 along the outside of the top portion of a cap-less test tube 11. The test tube 11 may have a circular ring 44 around the outside of the tube below the threads 23. The lower cup base plate 20 is generally thicker than the upper cup base plate 17 and supports the test tubes in a stable manner.

As depicted in FIGS. 1 and 4, the lower cup portion 13 also includes a generally circular lower cup lip 25 on an upper end of a substantially cylindrical lower cup side wall 27 surrounding an open top 26 of the lower cup portion. The lower cup base plate 20 is either attached to a lower end of the lower cup side wall 27, or the whole lower cup portion 13 is molded from a single piece of material, preferably a transparent plastic material so that the progress of the fluid can be monitored and any foreign materials or defects can be seen. If any foreign materials are detected, the collection device 10 should be discarded in favor of a new collection device, since such material may interfere with the laboratory tests to be conducted on the fluid samples. The entire upper cup portion 12 is preferably also molded from transparent plastic for the same reasons. Thus, the upper cup portion and the lower cup portion are each one-piece and made from a transparent or translucent plastic material.

Continuing with FIGS. 1 and 2, the upper cup portion 12 is removably insertable in the open top 26 of the lower cup portion 13. When the upper cup portion 12 is in the lower cup portion 13, the outside of the upper cup side wall 16 preferably rests against the inside of the lower cup side wall 27. The upper cup portion 12 is rotatable in the lower cup portion 13. The smooth finish of the preferred plastic material permits the upper side wall 16 to slide easily along the lower cup side wall 27. The plastic material also permits the upper cup portion 12 to adhere well inside the lower cup portion 13, even though the two portions nevertheless remain detachable, so the upper cup portion is unlikely to pop out of the lower cup portion during use, which would disrupt the lumbar puncture test. The upper cup base plate 17, which is above the lower cup base plate 20 when the collection device 10 is in use, has a smaller diameter than the lower cup base plate 20. The lower part (i.e., in the area of the upper cup base plate) of the upper cup portion has an outside diameter that is slightly less than an inside diameter of an upper part (i.e., in the lower cup lip area) of the lower cup portion, so the lower part of the upper cup portion fits closely into the upper part of the lower cup portion. By "slightly" is meant between about one and five millimeters.

As seen in FIG. 2, the slightly smaller upper cup portion 12 is designed to fit closely in the lower cup portion 13, preferably leaving a space 28 between the bottom of the upper cup base plate 17 and the top of the lower cup base plate 20. The space 28 facilitates rotation of the upper cup portion 12 in the lower cup portion 13, since there is no need to overcome friction between the two base plates 17, 20, as would occur if the space 28 were not present and the base plates were in contact with one another. The space 28 is also believed to increase the chances that the spinal fluid will not be contaminated by particles or other undesirable material that might otherwise collect between the two base plates 17, 20 if they were in contact with one another. When the collection device 10 is in use, spinal fluid drips down across the space 28 and through the test tube opening 21 immediately below the drain hole 18.

As illustrated in FIGS. 1 through 4, the upper cup portion 12 comprises a mechanism 30 for rotating the upper cup portion 12 in the lower cup portion 13, so that the drain hole 18 aligns with the openings 21 of the individual test tubes 11 attached in the lower cup portion. The rotation mechanism 30 includes a thumb lever 31, which is attached to the upper cup lip 15, preferably adjacent to the drain hole 18. The manually operated collection device 10 is designed to hold the standard number of test tubes used in a lumbar puncture testing, yet also be small enough to hold in one hand. The physician or other health professional administering the lumbar puncture can hold the collection device 10 in one hand, and rotate the upper cup portion in the lower cup portion using the thumb of the same hand. This leaves the physician's other hand free to perform other important functions.

As shown in FIGS. 1, 3, 4, and 5, the rotation mechanism 30 also includes a number of vertically oriented indentations 32 in the outside of the upper cup side wall 16, each of which corresponds to a vertically oriented ridge 33 in the inside of the lower cup side wall 27. The preferred plastic material the collection device 10 is made from is relatively flexible, which allows the ridges 33 to pop in and out of the indentations 32 as the upper cup portion turns. In use, the pressure of the operator's thumb (or other finger) pushing against the thumb lever 31 causes rotation of the upper cup portion 12, preferably counterclockwise, in the lower cup portion 13. Furthermore, the ridges 33 snapping into place in the indentations 32 causes a slight clicking sound, which signals the physician that a position has been reached. The physician therefore need not stare intently at the collection device 10 during the procedure and can concentrate on the patient. The indentations and corresponding ridges are spaced apart along the side walls 16, 27 so that when the ridges 33 are engaged in the indentations 32, fluid dripping through the drain hole 18 will fall into one of the test tubes 11 in the lower cup base plate 20. With thumb pressure on the thumb lever 31, the upper cup portion 12 will move to the next engagement position, where the drain hole 18 is aligned with an adjacent test tube 11, and so forth. The collection device 10 is thus "self-aligning".

A preferred embodiment of the collection device 10 includes four evenly spaced indentations 32 along the upper cup side wall 16, and four ridges 33 evenly spaced along the lower cup side wall 27, or vice versa. The thumb lever 31 preferably includes a gripping surface 34 so that even a wet thumb is unlikely to slip off, causing interference with the lumbar puncture test (see FIG. 2).

Figure 6:
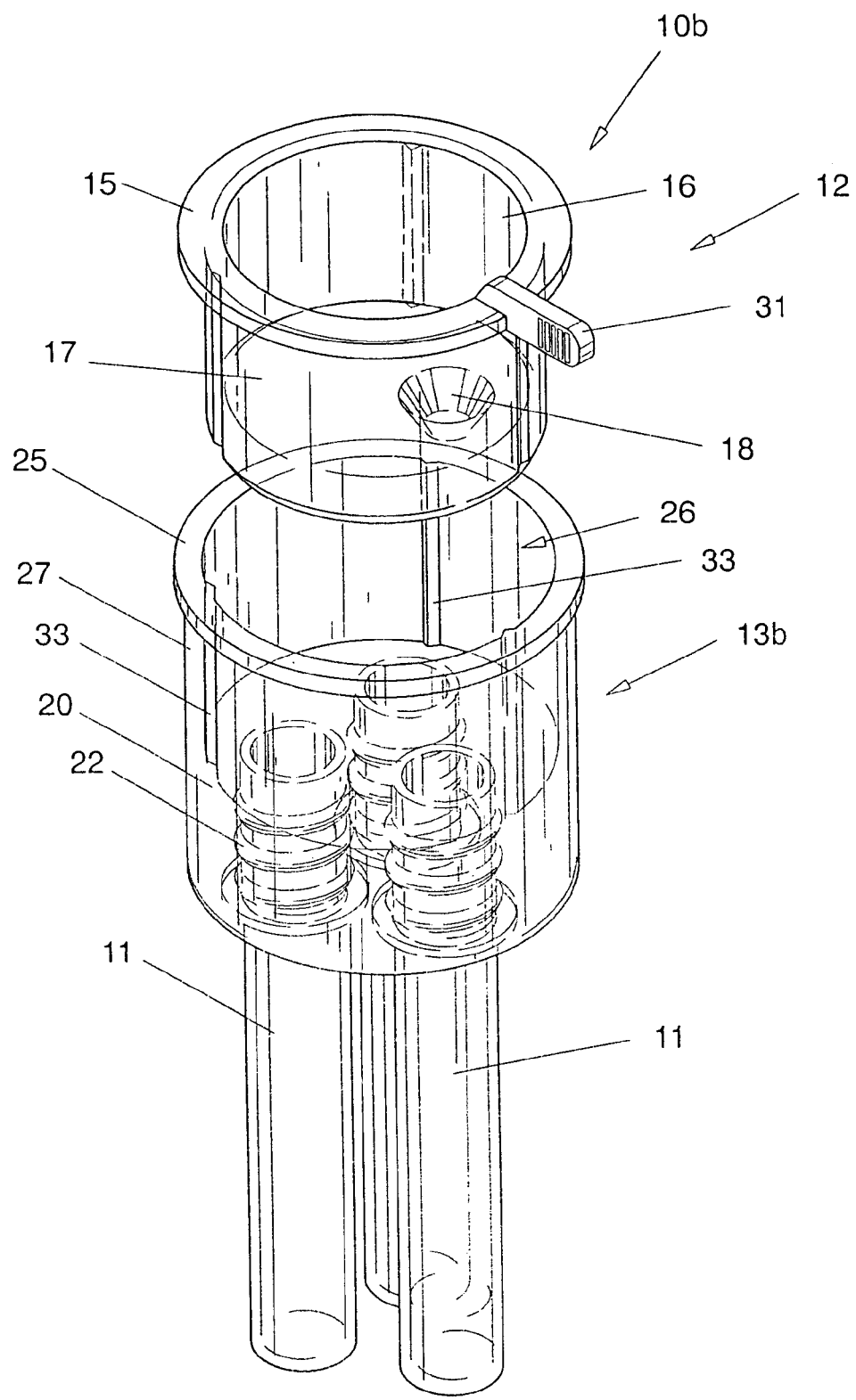
FIG. 6 is a perspective view of a pediatric lumbar puncture fluid collection device according to the present invention.

Turning to FIG. 6, a pediatric embodiment of the collection device 10b includes three openings 21 for three test tubes 11. In general, less spinal fluid is taken from children, since they are usually smaller than adults, so fewer test tubes are required.

Figure 7:
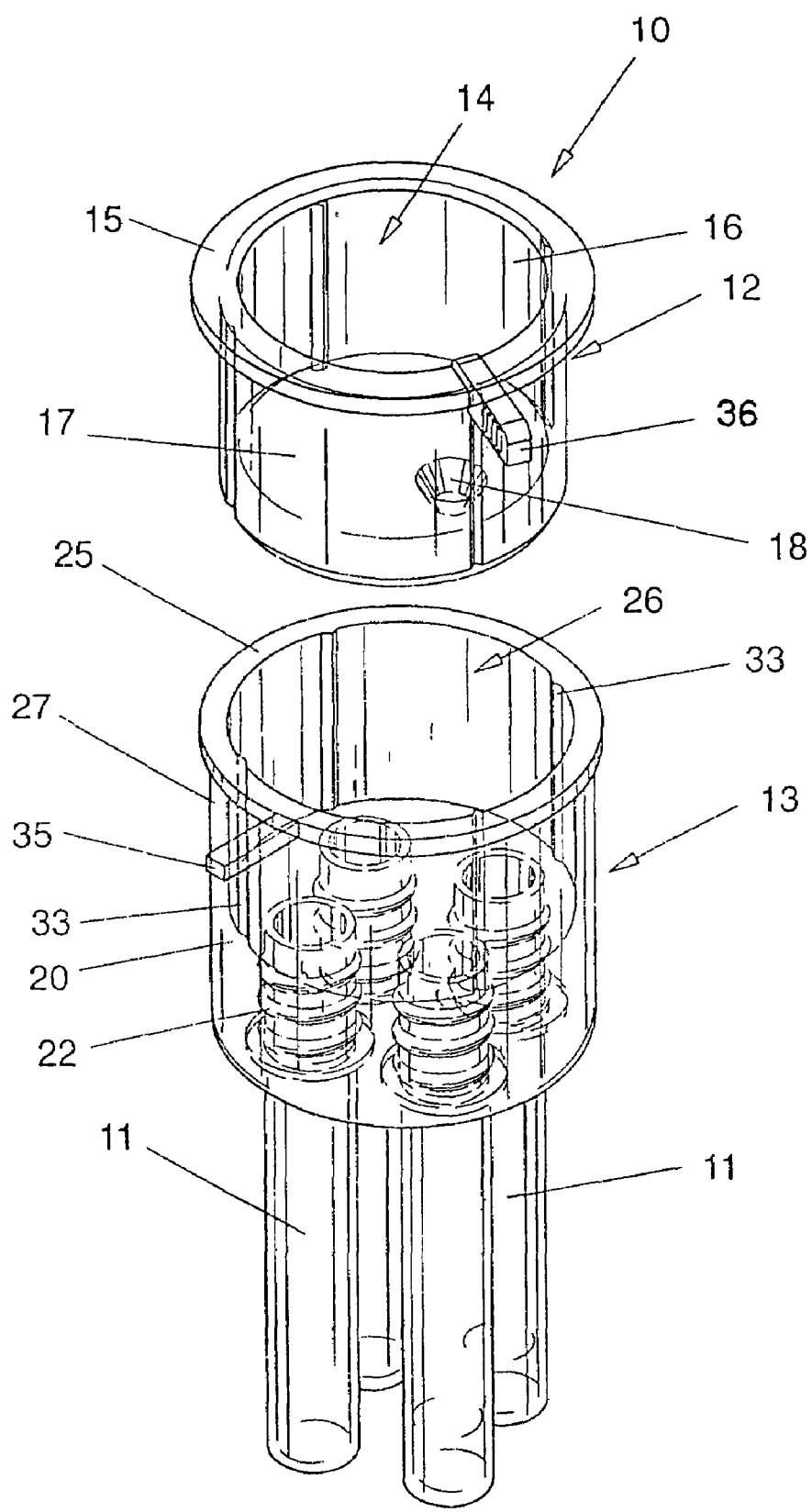
FIG. 7 is a perspective view of a lumbar puncture fluid collection device according to the present invention.
Figure 8:
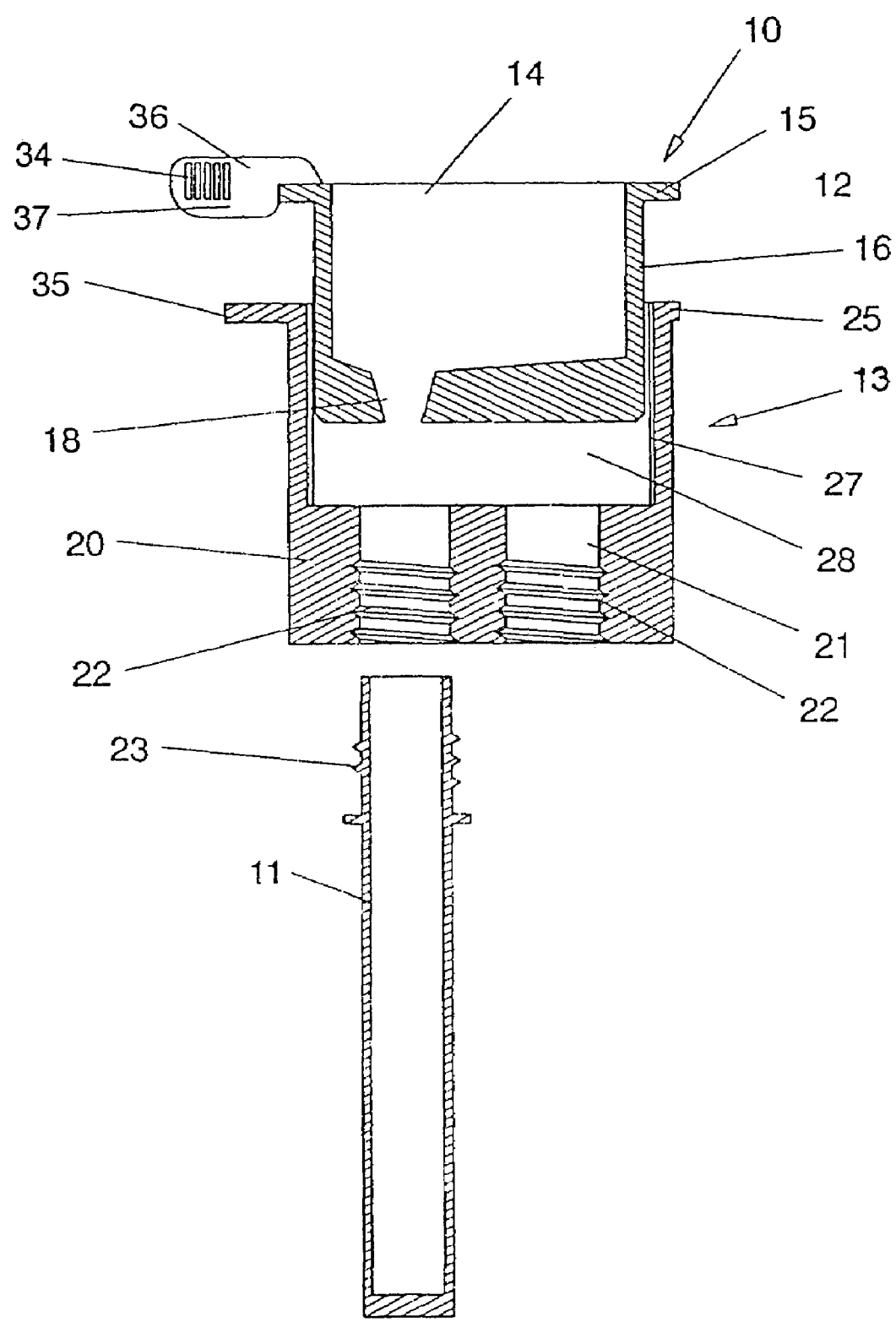
FIG. 8 is a cross-sectional, elevational view of a lumbar puncture fluid collection device according to the present invention, shown with a test tube.

Turning to FIGS. 7 and 8, an alternate embodiment of the collection device includes a stop 35 that extends out from the lower cup lip 25. An enlarged thumb lever 36 includes an extended lower section 37 that extends down from the enlarged thumb lever. When the extended lower section 37 of the enlarged thumb lever contacts the stop 35, the upper cup portion 12 will no longer rotate. This prevents fluid from dripping into an already full test tube. It also causes the upper cup portion 12 to rotate in one direction, counter-clockwise, so the collection device will not proceed in a wrong direction and interfere with the test tube samples. The enlarged thumb lever 36 can be turned into the stop 35 as the final position, which effectively closes the drain opening 18 from the test tubes 11.

Figure 9:
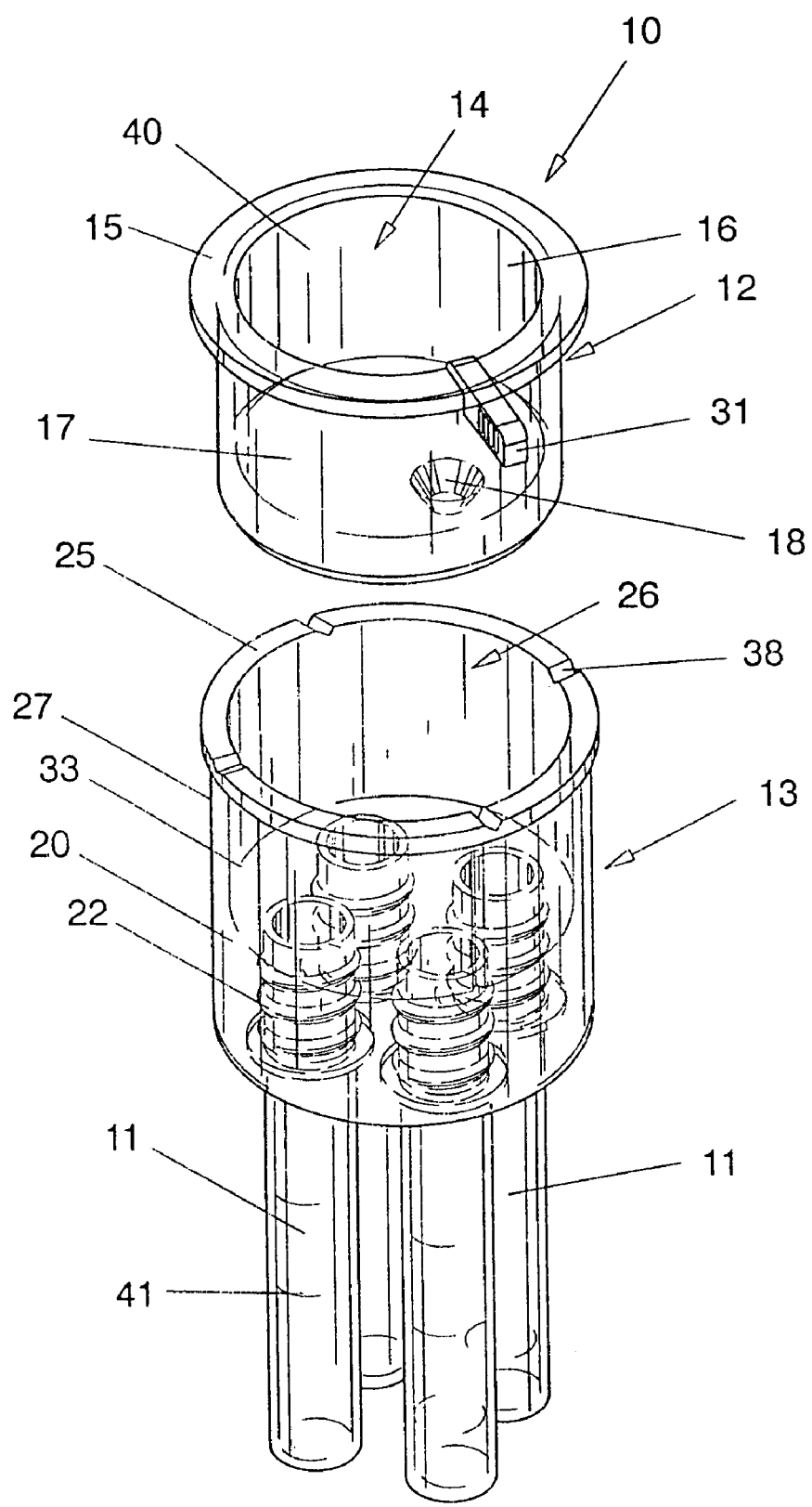
FIG. 9 is a perspective view of a lumbar puncture fluid collection device according to the present invention.
Figure 10:
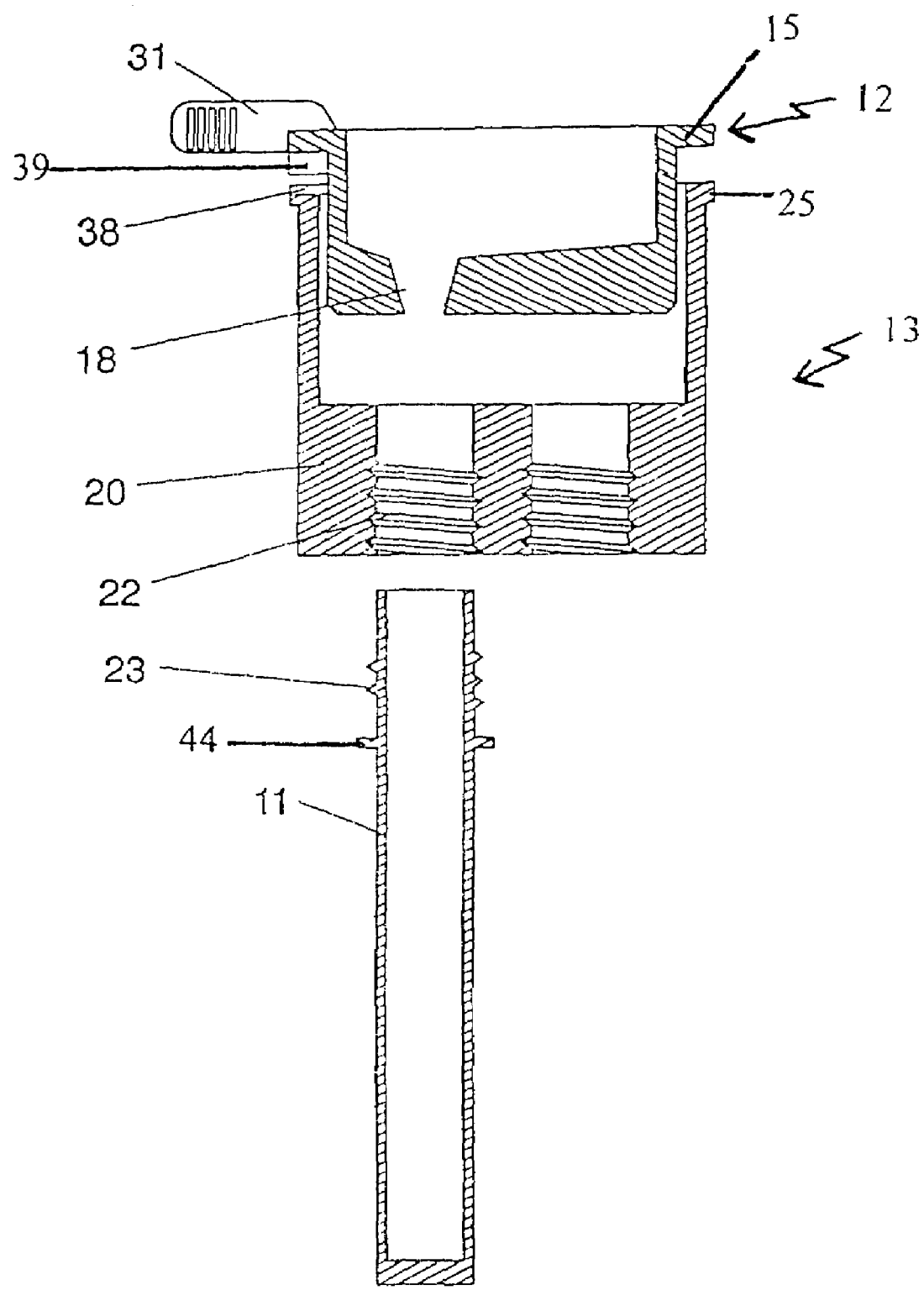
FIG. 10 is a cross-sectional, elevational view of a lumbar puncture fluid collection device according to the present invention.

In an alternate embodiment depicted in FIGS. 9 and 10, a bottom surface of the upper cup lip 15 is adjacent to an upper surface of the lower cup lip 25 when the collection device 10 is assembled. The upper cup portion need not be large (e.g., hold about ½ to one cup of fluid); a smaller upper cup portion 12 is shown in FIG. 10. This rotation mechanism 30 comprises a thumb lever 31 extending from the upper cup lip 15, a protrusion 39 under the upper cup lip 15 at the base of the thumb lever 31, and a plurality of (preferably four) spaced apart slots 38 in the lower cup lip 25. When the thumb lever 31 is pushed, the upper cup portion 12 rotates in the lower cup portion 13. The cup lips 15, 25 are correspondingly sized in order to facilitate this travel. This minimizes friction in the device assembly. When the protrusion 39 at the base of the thumb lever 31 clicks into one of the slots 38 in the lip, rotation of the upper cup portion is temporarily halted. The slots 38 correspond to the positions of the test tubes 11, so that the drain hole 18 is aligned with a test tube opening 21 at each slot position. Once the test tube 11 is filled with the desired amount of fluid, the user pushes the thumb lever 31 again until the protrusion 39 drops in to the next slot 38, which corresponds with the adjacent test tube, and so forth.

The collection devices herein may include a detachable cap 40, as shown in FIG. 9. The cap 40, which is preferably made of a transparent plastic, is removed and discarded prior to the lumbar puncture procedure.

The single drain hole 18 and rotation mechanism 30 allow the user to direct flow to the desired test tube and allows control over the amount of fluid that flows into each test tube. Each test tube optionally includes demarcation lines 41, as shown in FIG. 9. These help the physician fill each test tube 11 with approximately the same amount of fluid, if desired.

The collection device preferably includes a "closed" position against the stop, in which the drain hole 18 is not over any of the test tube openings 21. In this position, no fluid can flow into any of the test tubes, or out of the upper cup portion 12, since the drain hole 18 is closed off by the lower cup base plate. This "closed" position is approximately 360 degrees from the starting position and represents the preferred finishing position of the upper cup.

Since there are four spaced apart test tubes, the physician can set the collection device 10 on the examining/operating table without worrying about whether the collection device 10 will fall over. The collection device 10 holds the set of test tubes 11 together. The entire collection device 10 can be labeled, or each test tube can be labeled individually. The individual test tubes 11 can easily be unscrewed from the collection device 10 in the laboratory, as desired, without sloshing the contents out of the tube.

The collection device 10 is preferably included in a lumbar puncture tray. The two cup portions 12, 13 will fit into a plastic tray, and the three or four test tubes normally included in a plastic lumbar puncture tray can be screwed into the lower cup portion 13 prior to the procedure.

In use, the test tubes are inserted in the fluid collection device 10 either at the manufacturing plant or just prior to the lumbar puncture procedure, so the device is ready for use. Each test tube 11 is inserted by removing its cap, if it has one, and screwing its upper end into the correspondingly threaded opening 21 in the lower cup portion 13 of the device. The upper cup portion 12 is in place in the lower cup portion 13, and any cap 40 is removed from the collection device 10 to ready it for use. Since there are four test tubes, the collection device 10 can be placed on the table prior to labeling with the bottoms of the test tubes 11 contacting the table; no test tube holder is required. The physician or other health professional performs the lumbar puncture procedure, then lifts the collection device 10 up with one hand and holds it under the dripping fluid. When the first test tube is filled with the desired amount of bodily fluid, the physician manipulates the lever 31, preferably with his or her thumb, while continuing to hold the collection device under the dripping fluid, so that the fluid flows into the second test tube adjacent to the first test tube. This continues until all four (or three) test tubes contain fluid. The physician then places the collection device 10 back on the table and ends the procedure. The collection device 10 and/or the test tubes 11 may be labeled before or after the lumbar puncture procedure. The device/test tubes are then taken to the laboratory for analysis of the fluid.

Figure 11:
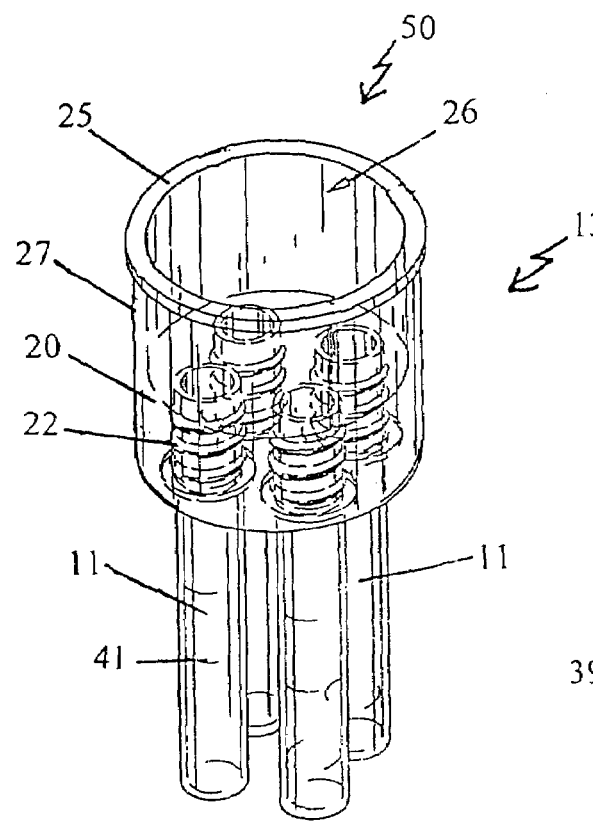
FIG. 11 is a perspective view of a lumbar puncture fluid collection device according to the present invention.

In yet another alternate embodiment depicted in FIG. 11, the collection device 50 is one piece rather than two piece. This simple, less preferred collection device 50 includes a cup-shaped portion with four spaced apart openings 21 in a circular base plate 20, and the physician merely turns the whole collection device 50 a quarter turn (for a four test tube device) as each test tube fills up. In use, the physician positions the dripping spinal fluid from the lumbar puncture needle or shunt over each test tube opening 21 in turn. This embodiment is advantageous in that it is less complicated and easier to use. It does not include an upper cup portion. One mold is sufficient for manufacturing this collection device, which does not require two separate cup portions. This device 50 may have three spaced apart openings 21 for accommodating three test tubes, which is useful for a pediatric lumbar puncture procedure.

It can be seen that the fluid collection device of the present invention may be used for collecting other types of bodily fluids, such as drainage from a swollen site or a shunt. Although it has been developed for use during a lumbar puncture procedure, the present collection device can be used for collecting bodily fluids during other medical procedures where samples are to be caught in test tubes for laboratory testing.

Figure 12:
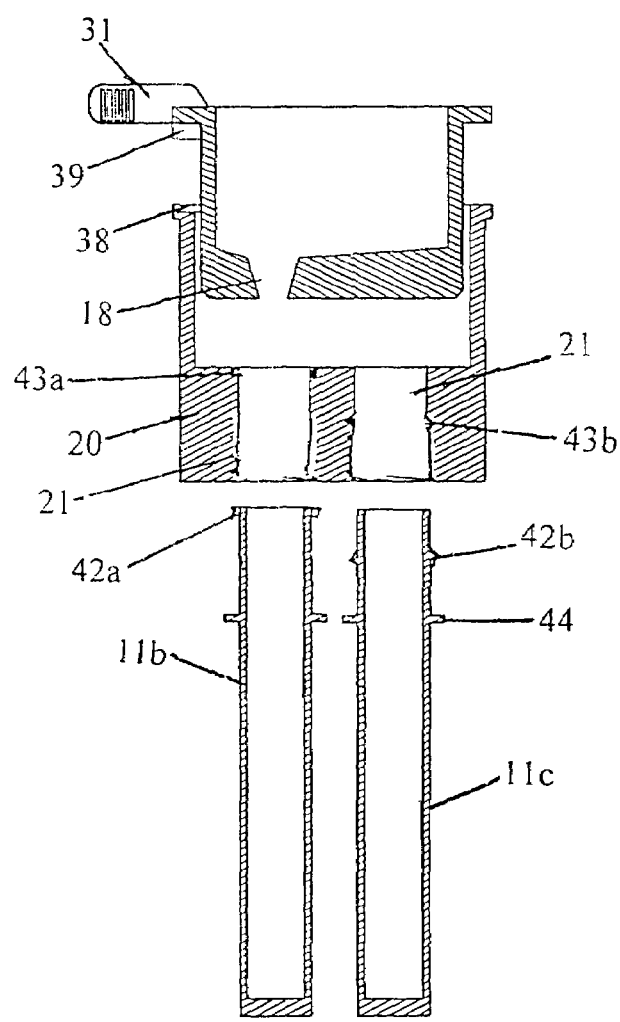
FIG. 12 is a cross-sectional, elevational view of a lumbar puncture fluid collection device according to the present invention.

As shown in FIG. 12, the test tubes need not be threaded at the top. Instead, each test tube 11b,c includes a male snap-in part 42 that corresponds to a female snap-in part 43 in the wall along the opening 21 in the lower cup base plate 20 of the collection device 10. The female snap-in part 43 may be at the top of the opening as shown on the left in FIG. 12 (43a on tube 11b), or midway along the opening 21, as shown on the right of FIG. 12 (43b on tube 11c). The position of the female snap-in part 43 along the opening 21 corresponds to the position of the male snap-in part 42 on the test tube 11b,c, which is preferably made of a relatively flexible plastic material. The male snap-in part may be square-shaped 42a, triangular-shaped 42b, a generally circular ring 42a in the wall around the opening, or any other suitable shape. There may be several male snap-in parts on a single test tube, and a corresponding number of female snap-in parts 43 in the opening 21 in the lower cup portion. The effect of the male snap-in parts 42 and corresponding female snap-in parts 43 is to allow the user to quickly snap the test tubes 11b,c into and out of the openings 21.

From the foregoing it can be realized that the described device of the present invention may be easily and conveniently utilized as a device for collecting bodily fluids. It is to be understood that any dimensions given herein are illustrative, and are not meant to be limiting.

While preferred embodiments of the invention have been described using specific terms, this description is for illustrative purposes only. It will be apparent to those of ordinary skill in the art that various modifications, substitutions, omissions, and changes may be made without departing from the spirit or scope of the invention, and that such are intended to be within the scope of the present invention as defined by the following claims. It is intended that the doctrine of equivalents be relied upon to determine the fair scope of these claims in connection with any other person's product which fall outside the literal wording of these claims, but which in reality do not materially depart from this invention. Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is:

1. A device for collecting spinal fluid during a medical procedure, the collection device comprising:
   a) an upper, generally cup-shaped portion comprising an open top, an upper cup side wall, an upper cup base plate at a lower end of the upper cup side wall, and a drain hole in the upper cup base plate;
   b) a lower, generally cup-shaped portion comprising an open top, a lower cup side wall, and a lower cup base plate at a lower end of the lower cup side wall, the lower cup base plate comprising a plurality of generally circular openings;
   wherein the upper, generally cup-shaped portion is removably insertable in and rotatable in the lower, generally cup-shaped portion, and the upper, generally cup-shaped portion comprises a rotation mechanism for rotating the upper, generally cup-shaped portion in the lower cup-shaped portion; and wherein the lower cup base plate openings are threaded for accommodating a correspondingly threaded end of a test tube.

2. The device according to claim 1, wherein the upper cup side wall is substantially cylindrical in shape, the lower cup side wall is substantially cylindrical in shape.

3. The device according to claim 2, wherein a diameter of the upper cup side wall is less than a diameter of the lower cup side wall, and the upper cup base plate is generally circular in shape and smaller than the lower cup base plate, which is also generally circular in shape.

4. The device according to claim 2, wherein the open top of the upper, generally cup-shaped portion is surrounded by a generally circular upper cup lip.

5. The device according to claim 4, wherein the open top of the lower, generally cup-shaped portion is surrounded by a generally circular lower cup lip.

6. The device according to claim 1, wherein the upper, generally cup-shaped portion and the lower, generally cup-shaped portion are each one-piece, and made of a transparent or translucent plastic material.

7. The device according to claim 1, wherein the lower part of the upper, generally cup-shaped portion has an outside diameter that is between about one and five millimeters less than an inside diameter of an upper part of the lower, generally cup-shaped portion.

8. The device according to claim 1, further comprising an enlarged thumb lever extending from the upper cup lip, and a stop that extends up from a lower cup lip of the lower, generally cup-shaped portion, the enlarged thumb lever comprising an extended lower section; wherein, when the extended lower section of the enlarged thumb lever is in contact with the stop, the drain opening is closed off from the test tubes and the upper cup portion is no longer rotatable.

9. The device according to claim 1, wherein a bottom surface of the upper cup lip rests on an upper surface of a lower cup lip of the lower, generally cup-shaped portion when the upper, generally cup-shaped portion is in the lower, generally cup-shaped portion.

10. The device according to claim 9, wherein the rotation mechanism comprises a thumb lever extending from the upper cup lip, a protrusion under the upper cup lip at the base of the thumb lever, and a plurality of spaced apart slots in the lower cup lip, each of the slots corresponding to a test tube position; wherein, when the thumb lever is pushed and the protrusion clicks into one of the slots, rotation of the upper, generally cup-shaped portion is temporarily halted.

11. A device for collecting spinal fluid during a medical procedure, the collection device comprising:
   a) an upper, generally cup-shaped portion comprising an open top, an upper cup side wall, an upper cup base plate at a lower end of the upper cup side wall, and a drain hole in the upper cup base plate;
   b) a lower, generally cup-shaped portion comprising an open top, a lower cup side wall, and a lower cup base plate at a lower end of the lower cup side wall, the lower cup base plate comprising a plurality of generally circular openings;

wherein the upper, generally cup-shaped portion is removably insertable in and rotatable in the lower, generally cup-shaped portion, and the upper, generally cup-shaped portion comprises a rotation mechanism for rotating the upper, generally cup-shaped portion in the lower cup-shaped portion; and wherein the rotation mechanism comprises a thumb lever extending from an upper cup lip of the upper, generally cup-shaped portion.

12. The device according to claim 11, wherein the rotation mechanism further comprises a plurality of vertically oriented indentations in the upper cup side wall, and a like number of corresponding, vertically oriented ridges in the lower cup side wall.

13. The device according to claim 11, wherein the thumb lever comprises a gripping surface.

14. The device according to claim 11, wherein the generally circular openings are threaded for accommodating a correspondingly threaded end of a test tube.

15. The device according to claim 11, wherein the drain hole is in a mid section of the upper cup base plate, and is funnel-shaped.

16. The device according to claim 11, wherein each of the lower cup base plate openings comprises a female snap-in part that corresponds to a male snap-in part on a test tube.

17. The device according to claim 16, wherein the female snap-in part is a generally circular ring.

18. The device according to claim 16, wherein the female snap-in part is generally triangular in shape.

19. The device according to claim 11, wherein an upper face of the upper cup base plate is sloped toward the drain hole.

* * * * *